US010319209B2

(12) United States Patent
Carlton-Foss

(10) Patent No.: US 10,319,209 B2
(45) Date of Patent: Jun. 11, 2019

(54) METHOD AND SYSTEM FOR MOTION ANALYSIS AND FALL PREVENTION

(71) Applicant: John Carlton-Foss, Weston, MA (US)

(72) Inventor: John Carlton-Foss, Weston, MA (US)

(*) Notice: Subject to any disclaimer, the term of this patent is extended or adjusted under 35 U.S.C. 154(b) by 0 days.

(21) Appl. No.: 15/613,623

(22) Filed: Jun. 5, 2017

(65) Prior Publication Data
US 2017/0352240 A1  Dec. 7, 2017

Related U.S. Application Data

(60) Provisional application No. 62/345,258, filed on Jun. 3, 2016.

(51) Int. Cl.
| | |
|---|---|
| *G08B 21/04* | (2006.01) |
| *G06N 20/00* | (2019.01) |
| *A61B 5/11* | (2006.01) |
| *G08B 5/36* | (2006.01) |
| *G08B 6/00* | (2006.01) |
| *G08B 25/08* | (2006.01) |

(52) U.S. Cl.
CPC ............ *G08B 21/0446* (2013.01); *A61B 5/11* (2013.01); *A61B 5/1116* (2013.01); *A61B 5/1117* (2013.01); *G06N 20/00* (2019.01); *G08B 5/36* (2013.01); *G08B 6/00* (2013.01); *G08B 25/08* (2013.01)

(58) Field of Classification Search
CPC ..... G08B 21/0446; A61B 5/11; A61B 5/1116; A61B 5/1117; G06F 3/017
See application file for complete search history.

(56) References Cited

U.S. PATENT DOCUMENTS

| | | | |
|---|---|---|---|
| 4,342,465 A | 8/1982 | Stillings | |
| 5,329,649 A | 7/1994 | Turek | |
| 6,207,190 B1 | 3/2001 | Richardson et al. | |
| 6,895,341 B2 | 5/2005 | Barrey et al. | |
| 7,280,040 B2 | 10/2007 | DeVaul | |
| 7,827,011 B2 | 11/2010 | DeVaul et al. | |
| 7,988,647 B2 | 8/2011 | Bunn et al. | |
| 8,101,599 B2 | 1/2012 | Shetty et al. | |
| 8,217,795 B2 | 7/2012 | Carlton-Foss | |
| 8,449,471 B2 | 5/2013 | Tran | |
| 8,460,219 B2 | 6/2013 | Miyake | |
| 8,461,988 B2 | 6/2013 | Tran | |
| 8,525,673 B2 | 9/2013 | Tran | |
| 8,525,687 B2 | 9/2013 | Tran | |
| 8,529,448 B2 | 9/2013 | McNair | |
| 9,028,405 B2 | 5/2015 | Tran | |
| 9,159,215 B1 | 10/2015 | Kusens | |
| 9,204,796 B2 | 12/2015 | Tran | |
| 9,351,640 B2 | 5/2016 | Tran | |

(Continued)

*Primary Examiner* — Laura N Nguyen
(74) *Attorney, Agent, or Firm* — Davis & Bujold, P.L.L.C.; Kimberly Peaslee

(57) ABSTRACT

A system and method of motion analysis, fall detection, and fall prediction using machine learning and classifiers. A wearable motion sensor for collecting and transmitting motion data for use in a fall prediction model using features and parameters to classify the motion data and notify when a fall is emergent. Using machine learning, the fall prediction model can be created, implemented, evaluated, and it can evolve over time with additional data. The system and method can use individual data or pool data from various individuals for use in fall prediction.

20 Claims, 9 Drawing Sheets

(56) References Cited

U.S. PATENT DOCUMENTS

| | | |
|---|---|---|
| 9,392,966 B2 | 7/2016 | Ten Kate |
| 9,489,820 B1 | 11/2016 | Kusens |
| 9,524,443 B1 | 12/2016 | Kusens |
| 9,549,691 B2 | 1/2017 | Tran |
| 9,568,594 B2 | 2/2017 | Harash et al. |
| 9,592,387 B2 | 3/2017 | Skelton et al. |
| 9,607,498 B2 | 3/2017 | Osorio |
| 9,626,566 B2 | 4/2017 | Versace et al. |
| 9,652,992 B2 | 5/2017 | Kaleal, III |
| 2006/0252999 A1 | 11/2006 | Devaul et al. |
| 2006/0282021 A1 | 12/2006 | DeVaul et al. |
| 2007/0010748 A1 | 1/2007 | Rauch et al. |
| 2009/0055176 A1* | 2/2009 | Hu .................. G10L 15/08 704/240 |
| 2011/0312473 A1 | 12/2011 | Chu et al. |
| 2013/0146088 A1 | 6/2013 | Takahashi et al. |
| 2013/0228394 A1 | 9/2013 | Sousa et al. |
| 2016/0155312 A1* | 6/2016 | Osorio ............ A61B 5/1117 340/573.1 |
| 2016/0369504 A1* | 12/2016 | Kim .................. E04B 5/43 |
| 2017/0046568 A1* | 2/2017 | Bulzacki ............ G06F 3/017 |

\* cited by examiner layout

— remainder of layout with some overlap for orientation

Accelerometer Module

Power Management

α = CORE OF COMMUNICATIONS NETWORK

METHOD AND SYSTEM FOR MOTION ANALYSIS AND FALL PREVENTION

CROSS REFERENCE TO RELATED APPLICATION

This application claims priority from U.S. Provisional Application Ser. No. 62/345,258 filed Jun. 3, 2016; the disclosure of which is incorporated herein by reference in its entirety.

FIELD OF THE DISCLOSURE

The present disclosure relates to wearable medical devices and more particularly to wearable medical devices used for motion analysis and fall prevention.

BACKGROUND OF THE DISCLOSURE

People fall and run into objects at all stages of life. These impacts place people at risk, the outcome of which may vary from no damage to death. An infant may be dropped, suffer permanent brain damage, stunted growth, and premature death. An eight-year old without a seat belt may suffer a severe concussion and permanent impairment in an automobile accident when his head hits the windshield. A high school basketball player may lose his balance and continue onward after a layup to crash into a wall behind the basket. A triathlon runner decompensates and falls as she approaches the finish line. A middle aged man damages his hand by tripping over an uneven panel in a concrete sidewalk while running to his car. A nonagenarian who still rides her bicycle misses a stair step, suffers a bad fall, and doesn't live to see the next day.

Considering the number and extent of impacts during childhood and earlier adult life it is a wonder that there is not more medical damage recognized. Yet life's earlier years are not marked as being a primary time of risk, perhaps because of the physical, neurological, occupational, and other plasticity of youth. However, as people age, they become more likely to fall and their body becomes more vulnerable so they become more likely to sustain significant injury when they fall. The healing processes become slower as we age and so we heal more slowly. Thus, the same injury can have a higher life impact for older people, and because the healing process takes time, a vicious cycle ensues leading the person to be weaker and vulnerable to additional falls.

SUMMARY OF THE DISCLOSURE

It has been recognized that technology is needed to detect when people are at heightened risk of falls, and to alert them or otherwise intervene, so that they can change their current or longer term behavior to avoid an emergent fall.

One aspect of the present disclosure is a system for detecting an emergent fall comprising one or more sensors wearable by a user, at least one of the one or more sensors being configured to collect and transmit motion data; a hub for receiving and labeling the sensor data, wherein labeling the data includes date/time and whether a subsequent fall actually occurred; a processor on the hub configured to classify the motion and other sensor data based, in part, on whether a fall is emerging according to a fall prediction model, and to store the data classification, wherein the labeled data is used to create one or more models, classes, features, and strings to be used in classification via supervised or unsupervised machine learning, and the one or more parameters include time duration and time placement for a string; the processor is configured to match output from the data classification with one or more parameters, features, and models from the fall prediction; a transmitter for transmitting information about the classification to an alert system and to a repository of data; and the alert system configured to send a notification that a fall is emerging based, in part, on a confidence level for a match to the one or more parameters, strings, features, and models from the fall prediction model.

Another aspect of the present disclosure is a method of detecting an emergent fall comprising providing at least one wearable sensor; measuring at least motion data with the at least one sensor; creating a fall prediction model, wherein the input for the model comprises at least the motion data; implementing the fall prediction model; comparing at least one string or feature of the data with at least one string or feature of the fall prediction model; creating a classification using the comparison of the data to the model; calculating the probability that a fall is emergent; calculating a confidence level for the probability that a fall is emergent; indicating whether the fall is emergent based, in part, on a classification; evaluating the model in real-time; evolving the model with additional data from the at least one sensor; determining if the fall is emergent; and communicating, if the fall is emergent, that the fall is emergent so that the fall can be prevented.

Yet another aspect of the present disclosure is a wearable for detecting emerging falls and an actual fall comprising a power source; one or more sensors wearable by a user, at least one of the one or more sensors being configured to collect and transmit motion data; at least one processor for classifying data received from the one or more sensors according to a fall prediction model; a hub configured to receive the classified data as well as information about the classification, and to transmit the information about the classification to an alert system; a communications system sending data and commands, as well as information contributing to the sending of alerts between the remote server, the local server and the one or more hubs; and an alert system for sending notifications when an emergent fall has been identified based on the classification by the fall prediction model.

One embodiment of the wearable for detecting an emergent fall further comprises a machine learning server to offload demand from the hub and to function as a data repository to optionally implement a Big Data-based approach to the creation and evolution of models, features, and parameters.

In some cases, the machine learning server runs in a communitarian mutual self-help mode with different views of the individual and group data: to enable mutual monitoring and help by participating users; to enable acceptable privacy by participating users; to enable monitoring and data acquisition by professionals serving patients; to enable record keeping of users; and to enable communications among the parties using the communitarian system.

One embodiment is wherein the at least one sensor is an accelerometer and the notification is in the form of an audio/video signal. A second embodiment is wherein the at least one sensor is an accelerometer and the notification is in the form of a tactual/vibratory signal.

In some cases, the system for detecting a fall further comprises a receiver for receiving labeled data from the local repository of data for use in generating or updating the fall prediction model.

In some cases, the method for detecting a fall further comprises adjusting threshold parameters to adapt the fall prediction model to modify the sensitivity of the fall prediction model. Thus reducing the number of false positive and/or negatives.

These aspects of the disclosure are not meant to be exclusive and other features, aspects, and advantages of the present disclosure will be readily apparent to those of ordinary skill in the art when read in conjunction with the following description, appended claims, and accompanying drawings.

BRIEF DESCRIPTION OF THE DRAWINGS

The foregoing and other objects, features, and advantages of the disclosure will be apparent from the following description of particular embodiments of the disclosure, as illustrated in the accompanying drawings in which like reference characters refer to the same parts throughout the different views. The drawings are not necessarily to scale, emphasis instead being placed upon illustrating the principles of the disclosure.

DETAILED DESCRIPTION OF THE DISCLOSURE

Figure 1:
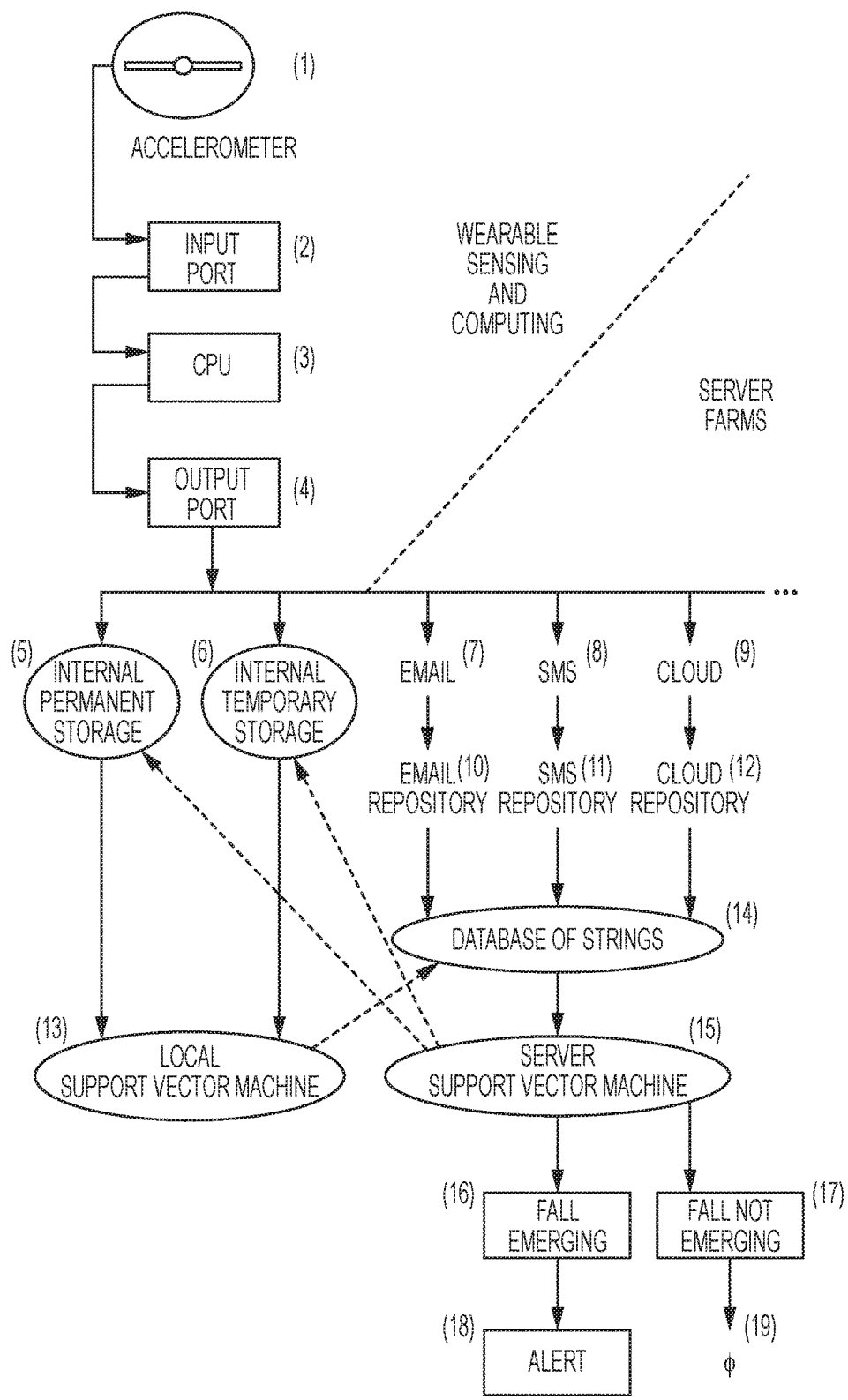
FIG. 1 shows a schematic of one embodiment of the system, with emphasis on the flow of information and logic, of the present disclosure.

One aspect of this disclosure is the detection of a sequence of dissonant correction steps, which are typically involuntary reactions to feeling out of balance while walking. Another aspect of this disclosure is a sudden loss of rhythm of body parts while walking or an alteration of the position and orientation of the body and its parts, indicating an impending fall.

Machine learning offers a permanent memory in the form of strings of sensor readings, with a preferred granularity of approximately 10 links per second. These strings comprise fall-related events as well as discernment of such events to enable an observer and also a victim to recognize such conditions that may lead to a fall and then intervene appropriately and early. A minor intervention can affect the prevention of a serious fall or an injury. Since different kinds of falls can have different precursors and time latencies ranging from seconds to hours or even days from a milestone to a fall event, a technology based on machine learning can initiate an appropriate intervention to the type of fall that would otherwise emerge. It is important to monitor falls and the propensity for and intensity of falls in an unobtrusive way well in advance of them becoming life threatening. Doing this makes early intervention possible by medical professionals who are then able to minimize the risk to the elderly. Possibly more important, it enables the gathering and using of information about individual people's emerging and evolving patterns of falling, stumbling, and near-falling using the innovative technology, herein described, for the purpose of preventing falls. It is also critically important to gather general data for groups and individuals about their falling processes to better understand the phenomenon.

The present disclosure collects data from individual people for the purpose of producing statistical classifiers, boost classifiers, and other kinds of machine learning devices to discern emergent falls of at least that same person. It then processes data through the at least one classifier, operating alone or in concert with other classifiers and machine learning devices, to discern emergent falls by that same person. The present disclosure also collects and stores data in a central repository comprised of data from individual people for the purpose of producing classifiers to discern emergent falls of all persons. The system then processes data through the single classifier or multiple classifiers working together to make a more capable classifier system, to discern emergent falls by various individuals. The first approach is highly tuned to individual differences. The second approach is attuned to the use of a general purpose system for all at-risk people. The two approaches are complementary, and optionally are operated in parallel, synchronously, and asynchronously.

Human bodies can be viewed very simply as waves or as particles. Viewed as waves, a human body under self-propulsion exhibits a number of characteristic frequencies that constitute normal balanced motion. Viewed as particles, human bodies conform to the laws of Newtonian physics. Without self-propulsion or other propulsion: momentum, angular momentum, and energy are conserved. Self-propulsion includes the pressure of the foot against surfaces, providing forces in forward, backward, sideward, and mixed or combined directions. Since, in a limited respect, the human body can be modeled as an inverted compound pendulum, sophisticated use of the foot, ankle, and other parts of the body enable a person to remain upright and moving.

Coordination is required at the level of the entire body and at the level of individual parts of the body. Thus, when people lose their balance enough to have to make a correcting move with one or more limbs, the reaction to that move is carried out to the other limbs, and is reflected in the bodily frequencies measured in many parts of the body. As humans age, such corrective events become more common, typically culminating in a fall that can be at least anticipated if not predicted.

A self-propelling human body can be modeled as existing and functioning in an N-dimensional Hilbert space. The entire body, as well as individual parts such as limbs, head and torso can each contribute dimensions with physical properties. The tangents, the first derivatives for each of the relevant properties with respect to each dimension, constitute tangent bundles in the smoothed manifold. The N-dimensional Hilbert space contains a complete, piecewise smooth representation of body motion, which is causal to the extent that all important dimensions are considered.

The system of the present disclosure predicts a fall and sends a signal to the user so that s/he can take appropriate steps to avoid the fall. Simple reasoning clarifies two extremes of this prediction. A year prior to a fall there may be risk of falling but very limited actionable non-zero prediction. Going to a physical therapist for strengthening and flexibility is one example of an action that could be used to avoid a future fall. At the other extreme, in the fraction of a second before impact a fall is already deterministic and happening, so the probability of falling is 100%. There, a user can still take action such as twisting to land on thick muscle or fat tissue to reduce risk of serious injury. A device, such as an inflatable balloon, can also be triggered, to reduce the impact of the fall. Also, in the infinitesimal fraction of a second indicating a fall has started, the probability of falling is 100%. In the infinitesimal fraction of a second before that, the probability of falling is less than 100%.

Thus, we consider a local statistical ensemble: a sub-manifold, differentiable almost everywhere, of many possible trajectories characterized in time as typically no more than about one minute before a fall event. This ensemble includes current physical measurements of such dimensions as the position, velocity, and accelerations of various parts of the body, as well as variations thereof. Different variants have slightly different probabilities of the person ending up in a fall event. The local ensemble characterizes the phase space trajectory of that type of fall sequence (type of fall). Thus at time $t_1$ there is a large number of possible outcomes, $N_1$, to the sequence, some of which may be falls. At later time $t_2$ some of these possible outcomes have been constrained out and others brought in from other local ensembles, leading to $N_2 < N_1$. At subsequent time $t_n$ some of these possible outcomes have been constrained out and others brought in from other local ensembles, leading to $N_n < N_{n-1}$. This summary can therefore be characterized as a numerical sequence that trends (not necessarily monotonically) toward a final N=2 (i.e., a fall or not a fall). One use of the system of the present disclosure then is to identify as early as possible which sequences are converging to N=2 with the value "fall." It is understood that the system may have other uses in addition to the N=2 application.

In the case of a long distance runner in a triathlon, for example, it may be dozens of minutes between a noticeable breakdown of form and the deep breakdown that leads the person to fall. However, it is only in exceptional cases, such as people fleeing for their lives, that such a trajectory or "string" would extend much longer. In this sub-manifold, we consider events that are very likely to lead to falls. In certain embodiments of the system of the present disclosure, devices map the extents of strings in the sub-manifold to possible outcomes. When the fall outcome is likely, that is, more likely than an optional parameter setting that establishes the desired threshold for a warning, the device gives the user a relevant alert, preferably with enough time to spare so that the person can act to avoid the impending fall.

In a general formulation there exists a larger sub-manifold of possible strings representing trajectories in phase space. When the system of the present disclosure detects that a person has reached a milestone point on a string that will terminate in a fall, it alerts the user, or initiates other actions to prevent the fall. In principle, there are many possible points in the sub-manifold of strings that can lead to a fall, and many following trajectories by which the fall can progress from that point.

One simple way to think of this is an electronic key and lock, analogous to a mechanical key and lock. When the pattern of the key matches that of the lock, the key unlocks the lock, and a defined action is taken. The electronic key and lock also is like the mechanical key and lock, in that more than one pattern can be used to unlock. In some cases, the device can be structured with a master key which is able to anticipate a multiplicity of possible falls with sufficient time in advance of the fall to allow for preventive action to be taken.

In another less general formulation there is a statistical ensemble of "behavior motions" that can be matched to N-dimensional event phase space "strings" in a database using a classifier, a boosted classifier, and/or other machine learning technology, and thereby implying that a person is about to fall or is at sufficient risk of falling, meaning that the risk is greater than the value of a parameter set by the manufacturer, the user, or someone else in machine learning and statistics, classification is the problem of identifying to which of a set of categories (sub-populations, classes) a new observation belongs, on the basis of a training set of data containing observations (or instances) whose category membership is known. An example would be assigning a given email into "spam" or "non-spam" classes or assigning a diagnosis to a given patient as described by observed characteristics of the patient (gender, blood pressure, presence or absence of certain symptoms, etc.). Classification is an example of pattern recognition.

In the terminology of machine learning, classification is considered an instance of supervised learning, i.e. learning where a training set of correctly identified observations is available. The corresponding unsupervised procedure is known as clustering, and involves grouping data into categories based on some measure of inherent similarity or distance. A classifier is a device and/or algorithm that implements classification, especially in a concrete implementation.

Sometimes different classifiers perform better in different domains, and/or multiple classifiers perform better each on their own domain(s) than a single classifier performing on the union of those domains. A boosted classifier, as summarized mathematically below, is currently one of the best means for performing classification over such a union of domains.

If the classifier system identifies a match with a high enough likelihood of an emerging fall, the device initiates an alarm or remedial action. Broadly, this is a many-to-1 relationship: many strings approximate to each possible behavioral motion. For example, people who internally experiences dizziness or imbalance while climbing stairs may pause or shift their weight back to the stair they are in the process of leaving. This behavioral motion may consume about one second or more before the person continues upward, and the person may or may not be conscious of the meaning. In this case an alert can be fed back to the user, and optionally a flag or other message can be sent to a larger tracking system that tracks the likelihood of a fall over periods such as hours, days, or months. In a more sophisticated version of the same device, the wavering of the users' body and mind can be detected as an alternative earlier "behavioral motion" that occurs while people step up or step on to the upper step. In this case an alert can be fed back to the user, and optionally a flag or other message can be sent to a larger tracking system that tracks the likelihood of a fall over periods such as hours, days, or months.

In general, note that false positives, leading to too many warnings, do not pose the same problem in fall prevention that they pose in automatic fall detection, because there is no costly Emergency Medical Team that will be called for an avoided fall. Instead the cost is one of distraction to the users and those with whom they live. While this cost may be acceptable when there is sufficient concern, they can be minimized at other times by a user-controlled sensitivity level parameter, so that there is no alarm for events that are unlikely to lead to falls.

Each string or position in a string in the statistical ensemble of strings (often located in terms of time) has its own likelihood of leading ultimately to a fall. In some embodiments there may optionally be at least one parameter that the user or a professional can set so that the technology responds when the desired likelihood is exceeded. In this manner, the device will be adaptively effective for a particular user and use. In certain embodiments, the system is self-correcting and capable of learning as it gains more experience so that the system can reduce the incidence of false negatives and false positives.

Throughout this discussion the general term "model" or "model/classifier" is used to describe any type of signal processing or analysis, predictive multivariate function estimation, statistical modeling, statistical learning, supervised learning, semi-supervised learning, unsupervised learning, and combinations thereof, as well as regression, classification technique, or other form of automated real-time signal interpretation.

There are general guidelines about falling. For example, lying horizontally in mid-air at a height of 2-3 feet, or more, as a result of a slip or fall has a probability close to one of a damaging fall. However, this probability is not exactly one for the general population because some people have body skills that enable them to curl and roll as they fall.

Individual differences in falling also exist. For example, a stumble may result in a fall for a person whose has weak ankles and slow reflexes and leg motions, whereas the same stumble will not lead to a fall for a person who is quick and strong. Similarly, swaying or wobbly walking will present a low likelihood of a fall for many people, although it will depend on the person and the degree of the motion. For a small percentage of people wobbliness is nearly a sure indicator that a fall is emerging.

Individual differences are important: different people are vulnerable in different ways, and therefore are likely to fall in different circumstances. Thus it is preferable for this system to be able to learn and respond to the movements of specific individuals as well as the movements of much larger populations. This attention to individuals fosters accurate discernment, while a large data repository from many individuals helps in early identification of behaviors that are likely to lead to falls, as well as a rapid approach to providing "typical" protection to a person who is vulnerable to falls.

Thus, it is desirable to identify the full fall ensemble and the sub-ensembles clustered around particular kinds of falls for the general population, for relevant sub-populations, and for individual people, so that machine learning can be used to identify emerging falls and intervene in effective ways before a fall becomes deterministic.

A predictive model is created by capturing and storing strings of automatically-indicated (and subsequently validated) movement data leading to a fall as well as user-indicated data (e.g., with the use of a help button that is subsequently validated). In some cases, the labeled raw data is stored in a buffer on board the person and later transferred to a repository. Optionally, the data is prepared on board the person or as part of being stored in the repository by manicuring and transforming the data to a form for optimal use in machine learning and recognition. One example of manicuring and transforming is projecting each string to the minimum dimensions necessary. Movement details are captured and stored along with other information including an evaluation of whether there was a fall, and if so, what kind of fall it was. The data can be gathered and stored during typical movement events as the person functions in their daily life. This data then accumulates into a statistical data bank that can be used by machine learning to detect likely falls long before they happen.

Machine learning methods such as statistical classification can also be used to perceive the environment, and initiate at least one such intervention including sending a warning when there is a heightened risk. An example of this would be production of an alert notification when people are walking or jogging toward a severely uneven panel in a cement sidewalk, so that there is heightened risk of a trip-and-fall. In one embodiment, a camera on the forward-facing side of the person captures and stores images of terrain ahead in the path including sidewalks where users walk. The classifier uses picture recognition to compare this flow of images to its learned set, and alerts the user when it identifies a surface likely to trip the user.

A machine learning method is inherently different from an approach in which a "fall" is indicated when a person's center of mass hangs out beyond a circle of stability at or beyond the furthest extremity of their feet. Such a configuration leads to a correction step or a stumble-and-recovery motion for a healthy person. In contrast, this could result in an actual fall for an impaired person who is not as able to recover from such an event. Such an approach is deterministic with a short warning time. This determinism is relevant only to those people whose condition makes them particularly vulnerable to the imbalance criterion indicating high risk for a fall.

By shifting to a statistical approach, emerging falls can be detected much earlier. Ideally, the fall is detected in time to interrupt actions that are leading to the emergent fall. For example, ambulatory elderly persons may begin tottering increasingly from side to side as they walk forward, culminating in a fall. The goal of preventive intervention is to interrupt predictable patterns or progressions in time so that they do not progress all the way to the type of fall that risks physical damage.

In one embodiment of the disclosure, a wearable device for a remote monitoring system positioned on the body of a person includes a data receiver to receive sensor data transmitted from at least one 3-D accelerometer, or equivalent, positioned on the person. Since fall precursors may take many forms, data capture preferably includes the inputs from a bank of unobtrusively placed sensors such as one or more well-placed accelerometers, altimeter, tilt monitor and gyroscope to detect and document contexts of accelerometer readings. In certain embodiments, a brain wave monitor may be used to detect dizziness or other disorientation. In some cases, the self-perception of dizziness may be accurate, but it may be a distraction. Thus, machine perception of disorientation may provide important real-time validation and verification for the user. In one embodiment, the wearable device further includes an analysis subsystem to take the data as input. The analysis subsystem analyzes the data and generates a report, one copy of which may be stored locally for local use. The wearable device may further include a transmitter to transmit and report to an external device to be used for more general purposes. In both cases, the report contains key information used in local or remote machine learning to predict falls.

In an alternative embodiment of the disclosure, the analysis subsystem of the wearable device further includes or develops at least one stored model of movement that is characteristic of each particular condition. In certain embodiments, the analysis subsystem uses the at least one stored model to analyze the data. In a further alternative embodiment, the at least one stored model holds data characteristic of an emergent fall, e.g., one that is likely to occur within the forthcoming at most 30 seconds. In some cases, an emergent fall is likely to occur significantly longer than within the forthcoming 30 seconds. Accordingly, the remote monitoring system can determine whether the wearer of the wearable device is likely to fall, by recognizing movements that are precursors of an emergent fall.

An illustrative example is provided by output from an accelerometer worn by an elderly person in good shape loosing balance while walking up a flight of stairs. At first he goes up stairs taking steps every second with a gyroscope pointing vertically in his torso's frame of reference. After several steps he experiences subjective loss of balance, briefly pauses, and shifts his weight back to the stair he was leaving. During this adjustment time, depending on how much he loses his balance, the gyroscope may deviate 0.1 radians/sec plus or minus from its original reading. Placing his foot back on that lower step, it makes a lower impact contact. The user then pauses on the lower step while regaining his sense of balance, and proceeds upward at his original pace. Deviations in accelerometer readings, pace and gyroscope readings provide dimensions for classification. The classifier then compares the details of this event with the data for the available classes of falls and near-falls, identifying the best match, and provides a numerical value, such as the class posterior probability, characterizing the event. For this specific case, the user is sent a low level alert by the device because the pause was moderate and the tilt non-existent. A significantly longer pause would trigger a higher level alert, and a verbal message to advise the user to take time to restabilize. In one embodiment of the system of the present disclosure, a summary report of the event is sent electronically to a doctor, any caretakers, and the user. The raw data is sent as another report to the repository tagged for this user.

In another embodiment of the disclosure, the wearable device provides an indicator of how closely the sensor data matches data of the at least one stored model. This indicator enables caregivers to interpret the report generated by the wearable device. In this way, the wearable device performs data classification. In some cases, the wearable device computes the class posterior probability, which gets its name from Bayesian statistics where the probability that an event fits into a particular class is referred to as being "posterior." given the observed data and a model for each class.

In a first arrangement, the at least one sensor of the wearable device is at least one 3-D accelerometer. Embodiments of the wearable device of the present disclosure typically include a data log for retaining collected data for monitoring the wearer of the wearable device over a period of time. At least some portion of every embodiment must be wearable to effectively monitor moving, ambulatory people.

In a first arrangement, the collected data is raw data or filtered, manicured, and/or transformed data from the at least one sensor. In a preferred embodiment this consists of raw data stored in a pre-fall log and a post-fall log after the user suffers a fall. These contents are transferred verbatim along with a label that they were associated with an actual fall. More generally, the threshold parameter for data collection is set such that data is collected for near-falls, and labeled accordingly. A string in the repository may be completed by manicuring redundant, extraneous parts such as the dozen steps in tempo up the stairs after the imbalance event. A string may also require transformation, such as between the earth frame of reference and the frame of reference of the person's torso, or between the frames of reference of two different sensors.

In a second arrangement, the collected data is analyzed data from an analysis subsystem. The data log enables a person to be monitored over a period of time. Once data has been collected, the wearable device transfers the contents of the log to at least one repository for further processing or forwarding depending on the configuration of the system. The length of monitoring prior to a fall or to another definable event is limited only by the buffer size available for the pre-fall and post-fall logs. In the earlier example of climbing stairs, the key event is the back-step taken by the user for rebalancing, and the key features for that event are its duration and quietude relative to continuing climbing. Intuitively, durations of less than 0.5 seconds are unlikely to imply an emergent fall, because the recovery time is substantially zero, so that a threshold that low would likely lead to excessive number of false positives in daily operations. Durations in excess of 5 seconds are likely to indicate a more serious condition such as significant lack of physical coordination, lack of stamina, pain or bodily damage, or a serious balance problem. In other words, the user requires a lengthy period of time to recover. In this example false positive and negatives will appear between 0.5 second and 5 second pauses, false negatives closer to 0.5 seconds, false positives closer to 5 seconds.

Certain embodiments of the system of the present disclosure are based on classification of strings into classes, and those classes determine thresholds. In this kind of data-based reasoning, intuition serves as an educational tool and also as a check to make sure a result makes sense. The threshold for warning about a likely fall for a particular user is determined by the data processed up to the time of the event for the user and optionally for similar people. Since the purpose of the disclosure is the avoidance of falls, and since the cost of a false positive is small (a false alarm and report), the biases in the system are made in the direction of producing false positives.

In another embodiment of the disclosure, a wearable device for a remote monitoring system includes a data receiver to receive data from at least one accelerometer positioned on a person wearing the wearable device. The wearable device further includes an analysis subsystem to take the data as input, the analysis subsystem including at least one stored model of emergent fall characteristics, the analysis subsystem analyzes the received data using the at least one stored model to determine if the person is likely to have a fall and at least one means to alert at least the wearer that s/he is likely to fall and needs to take appropriate action to avoid a fall.

The analysis subsystem further includes at least one data classifier to analyze the received data with regard to the at least one stored model. Since the analysis subsystem uses multiple classifiers over multiple domains containing different types of motions of the human body (e.g., an escalating sway is different from a balance step), those classifiers are teamed in a particular way, to produce a stronger classifier. Mathematically, the stronger classifier $H(X)=\text{sign}(\alpha_1 h_1(X_1)+\alpha_2 h_2(X_2)+\alpha_3 h_3(X_3)+\ldots)$, where $\Sigma\alpha_i=1$ and the $h_i(X_i)$ are strong in their own domains, $X_i$, but comparatively weak classifiers in other domains within X, a differentiable manifold on a Hilbert space. Each $h_i(X_i)$ may be based on nearest neighbor, neural network, support vector machine (SVM) or other classification mechanism. Note that H(X) simplifies to $h_1(X_1)$ and X simplifies to $X_1$ when only a single classifier is used in this boost classifier. Thus, classification typically refers to H(X) with one or more contributing classifiers, and because of the broad applicability of the mathematics, therefore applies to classifiers and classification in a broad set of domains, which may include those constructed from nanotechnology including emerging nanocomputation, chemistry, mechanics, brain science, electronics, and computer science including emerging quantum computers.

In a first arrangement, the model incorporated in the wearable device is organized into data classes and the data classifier, H(X), determines whether a fall is likely to take place by determining the at least one data class of the received data. In a second arrangement, the wearable device calculates features and derives strings from a data stream and applies Bayesian or other statistics to determine whether there a match to the stored models that indicate an impending fall.

In certain arrangements, the transmitter in the wearable device is a short-range transmitter. In another arrangement, the fall prediction system includes a wireless local area network connecting the wearable device and a near-by receiver console, which in turn optionally connects to a remote server. The wearable device transmits the report to the receiver console over the wireless local area network. In yet another arrangement, the fall prediction system includes a wireless wide area network connecting the wearable device and a receiver console, possibly a transmitter-receiver to the Cloud, for example. The wearable device transmits the report to the console over the wireless wide area network. Because it is common for organizations to make available such wireless wide-area networks and some municipalities make WiFi networks ubiquitously available for general use, the system can have broad application. A less reliable version of such a ubiquitous network is that offered informally in densely populated areas by Internet users who leave their routers unsecured. In a further arrangement, the fall prediction system includes a wireless connection to the Cloud.

In an alternative embodiment of the disclosure, both the wearable device and any other local part of the fall prediction system include a mobile source of power whereby the fall prediction system is usable away from a fixed location. The wearable device and optionally any console or connection point may include a locator device to provide, on one hand, information about the location and orientation of the person being monitored in the event that more extensive data is being gathered to understand further details of how the wearer moves, how the wearer falls and what injuries are likely, and on the other, definitive information about the distance between the person and the console or connection point.

In FIG. 1 the output of the accelerometer (1) is read into a CPU (3) where it is optionally filtered and analyzed, and passed on to the output subsystem (4) where it is sent internally to local permanent storage (5) or local temporary storage (6), and/or sent by email (7) to a repository for email (10), by SMS (8) to a repository for SMS messages (11), and/or by radio (9) to the Cloud (12). Note that radio includes connectivity to a wireless local area network and/or wide area network, and may include other modalities such as email.

Still referring to FIG. 1, individual data stored internally to the wearable device is analyzed and processed by a local support vector machine (SVM) capability (13), or other classification mechanism (SVMO), preferably in the embodiment of a proprietary application specific integrated circuit (ASIC) or an SVM server. In machine learning, SVMs are supervised learning models with associated learning algorithms that analyze data used for classification and regression analysis. Given a set of training examples, each marked as belonging to one or the other of two categories, an SVM training algorithm builds a model that assigns new examples to one category or the other, making it a non-probabilistic binary linear classifier. The same process can also be implemented for classification with more than two categories, potentially including, for example, various classes of near falls. An SVM model is a representation of the examples as points in space, mapped so that the examples of the separate categories are divided by a clear gap that is as wide as possible. New examples are then mapped into that same space and predicted to belong to a category based on which side of the gap they fall.

General data, including that from many wearers, is stored in a database of strings (14), preferably labeled, all or part of which may be viewed as training data, where it is operated upon by the SVM server (15), or other classification mechanism, to effectuate models to be used by many users. The SVM server is fast enough and receives enough data to modify results in real time. Flexible architecture enables the SVMs to be able to operate with data from any and all selected repositories. The individually worn systems are wearable computing. For reasonably scaled up implementations, the SVM servers participate in Server Farms. The output of the SVM (15) is a binary classification that the observation is either in the class indicating an emerging fall (16), along optionally with one or more probabilities, or in the class not indicating an emerging fall (17), along optionally with one or more probabilities. In the former case, notification is given in such form as an alert, an alarm, and/or a message to an external system.

One embodiment of the motion analysis system includes a wearable configuration of accelerometers and data analysis subsystems and further includes data models for interpretation of the data collected by the sensors. The motion analysis system monitors the activity and movements of a person with a wearable monitoring device. In one embodiment, the data analysis subsystems use the data models to determine whether the person is at high risk of falling. Some embodiments provide useful displays to the user, where the displays are based on algorithms operating on and displaying raw data alone and combined with derivative data.

The systems described herein for monitoring, interpretation, and proactive communications applications have at their foundation a combination of sensing, real-time statistical analysis, and wireless communications technology. Furthermore, this technology is packaged in a manner that is as comfortable and non-invasive as possible, and puts little additional physical or cognitive burden on the user. The systems are robust and reliable, unobtrusive, accurate, and trustworthy. In general, the systems are as simple as possible to operate, and difficult to break. A feature of the systems described here is the proactive, robust notification capability provided by the combination of sensing, real-time statistical analysis, and proactive communications.

Figure 2:
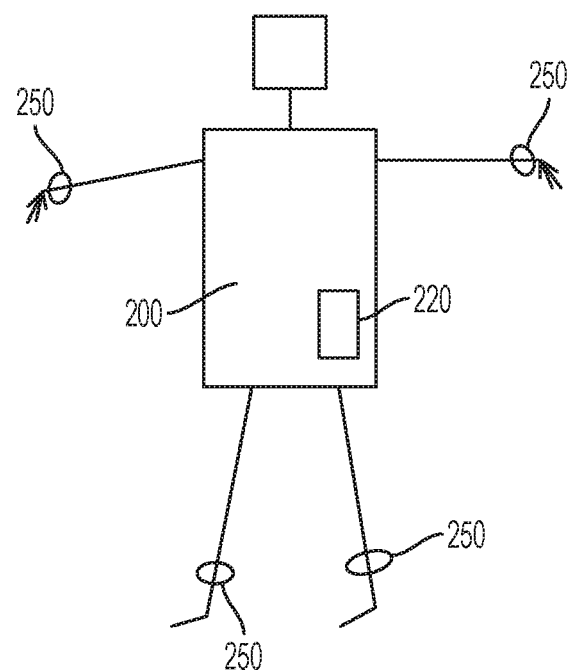
FIG. 2 shows a block diagram of a configuration of the optional sensor placement on a human figure according to principles of the present disclosure.

FIG. 2 is a block diagram of a configuration of the optional sensor placement on a human FIG. 200 according to principles of the disclosure. The human FIG. 200 is shown wearing 220 a core sensor including, but not limited to, one or more of the following including an accelerometer, a gyroscope, a tilt meter, an altimeter somewhere on the torso (e.g., in a shirt, blouse, or pants) and/or, for a more complicated analysis, accelerometers and optionally other sensors 250 at the wrists and/or ankles.

Figure 3:
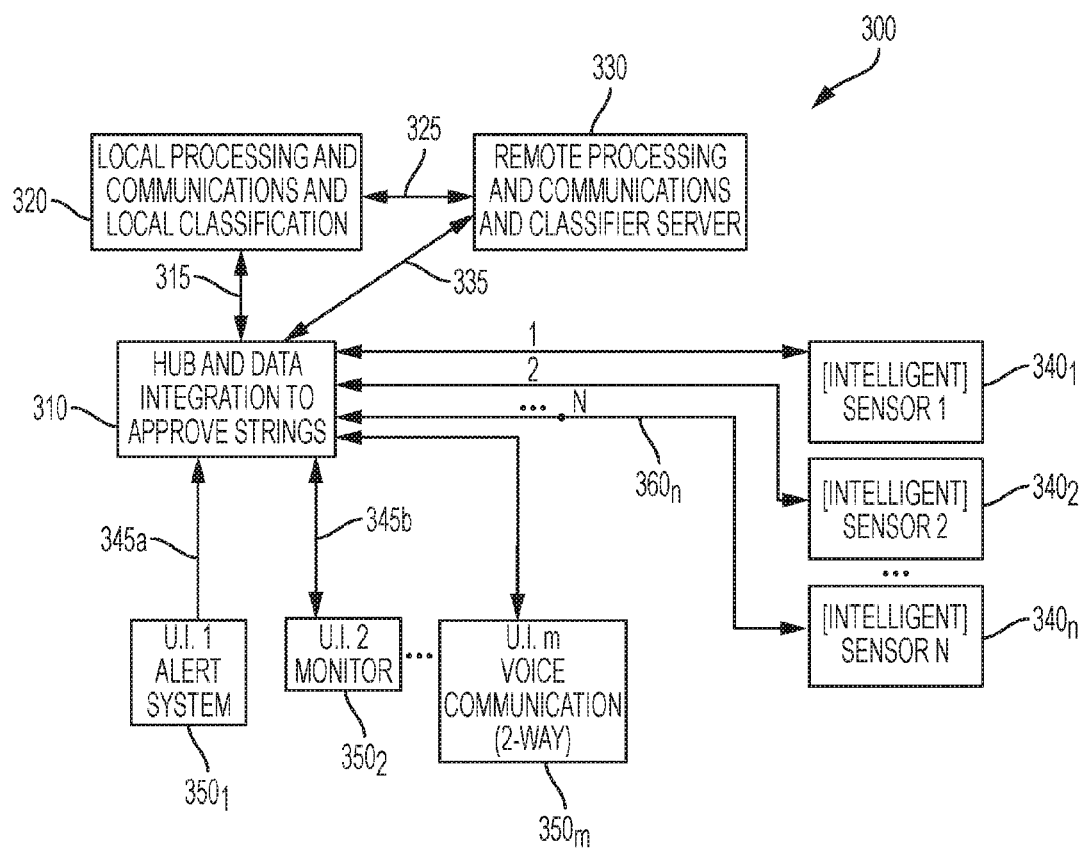
FIG. 3 shows a block diagram of the hub, user interfaces, server, and sensor network according one embodiment of the present disclosure.

FIG. 3 is a block diagram of the hub, server, and sensor network 300 according to one embodiment of the present disclosure. The hub and sensor network 300 includes a hub with data integration system (to convert N sensor streams into a synchronized m-dimensional string) 310 connected through a wired or a wireless connection 360 to as many as N sensor(s) 340, at least one of which is preferably located within the hub. In one embodiment, the sensor(s) streams data constantly whether the device is in acquisition mode to create or update a model, or in monitoring mode to anticipate high risk of a fall. In another embodiment, data is not initially collected from all sensors, but rather there are criteria based on a subset of sensors that lead to communication through the hub to start to capture a stream of data from additional sensors. In a preferred embodiment there is a single accelerometer (that is, N=1) that is physically located in the hub assembly. In alternative embodiments one or more sensors are located on the torso, the hip, and/or an extremity.

Still referring to FIG. 3, the hub 310 is connected to a portable wireless communications device 320, such as a cellular telephone, through a second wireless connection or network 315. The hub 310 is further connected to an external local area network (LAN) or external computer system (classifier server, for example, in the "Cloud") 330 through a wired or wireless connection 335. This connection is two-way to enable real-time sensing and classification through the hub and classifier server in desirable situations, such as when the processing demands may exceed the limits of the processors on the person or when the method explicitly relies on Big Data means. The connection from the External Classifier Server 330 enables updating of the hub/classifier 310 and other components such as sensors 340, providing new classifiers and parameters to the hub 310 and other components, and real-time classification with alerts and alarms sent to the hub and other subsystems. The hub 310 is further connected to user interface peripherals 350 through a wired or wireless connection 345. The wearable communication device 320 and external computer system 330 are connected through a wired or wireless connection. Note that, as above, in some embodiments two or more of these blocks are combined into one, such that, for example, Sensor 1, 340(1), is included in the hub 310.

In operation, the hub 310 communicates with and receives the continuously streaming output of the one or more sensors 340, enabling the sensors 340, to collect data and to transmit the collected data to the hub 310. The hub 310 also communicates with and controls the user interface peripherals including the alert/alarm system 350(1) and the user/administrator monitor 350(2). The hub 310 further communicates with portable devices such as the local processing unit 320 and with external network or computer systems 330. The hub 310 communicates data and data analysis to the peripherals 350, portable devices 320 and external systems 330.

The hub and sensor network 300 shown here is merely an example network. Alternative embodiments of the disclosure include a network 300 with fewer or more and/or different types of sensors, for example, including a network 300 with only one type of sensor. Further alternative embodiments include a network 300 with hub and data integration 310 connected to only a local processing unit with classification 320. In communitarian embodiments (See, for example, FIG. 9) there may be user interfaces 350 dedicated separately to such people as caretakers and medical professionals, whether connected directly to this hub and sensor network 300 or through a separate data and communications server. In still further alternative embodiments, the various devices in the network 300 are able to communicate with each other without using the hub as an intermediary device. In short, many types of hub, sensor, communications devices, computer devices and peripheral devices are possible within the scope of the present disclosure. The present disclosure is not limited to those combinations of devices listed here.

Figure 4A:
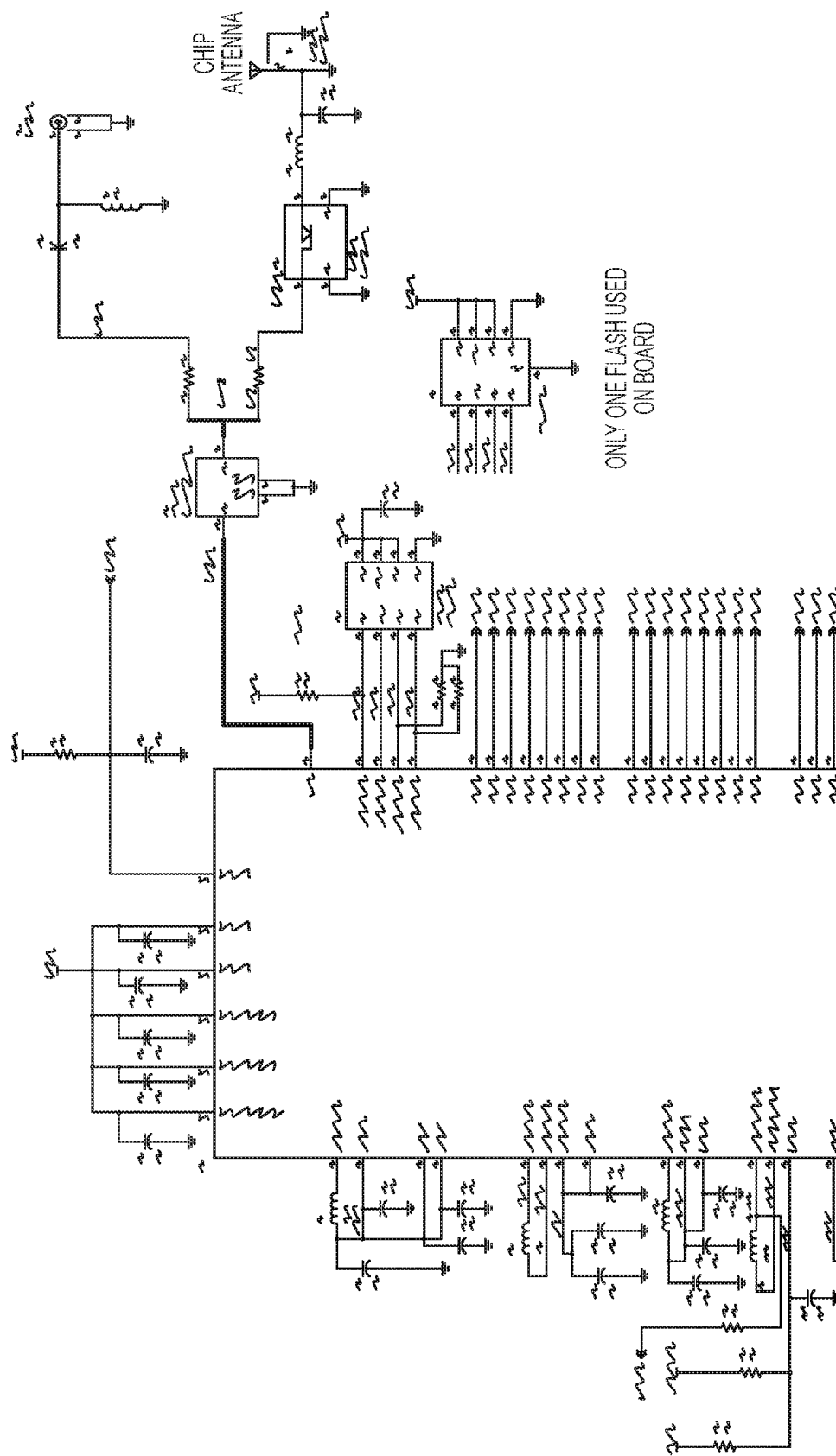
FIG. 4A and FIG. 4B are schematic diagrams of a conventional hub.
Figure 4B:
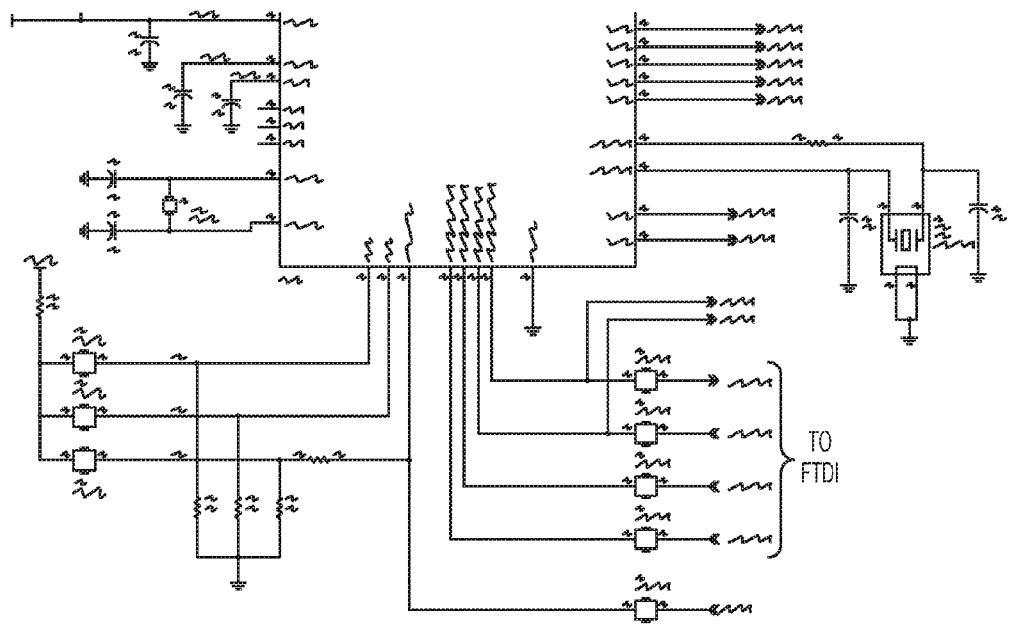
Figure 5:
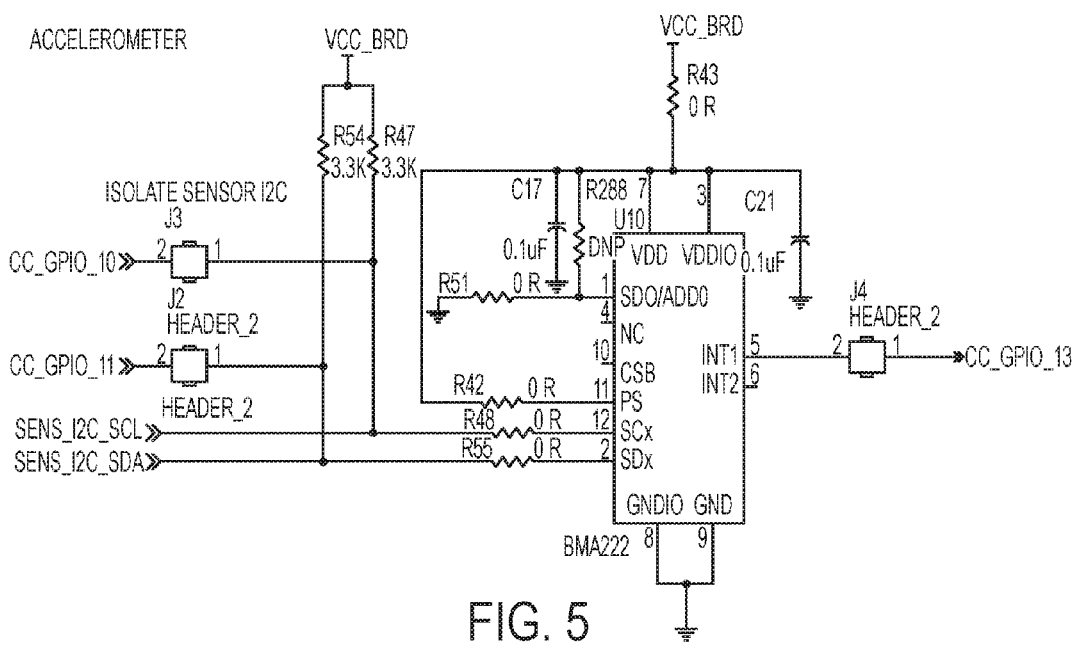
FIG. 5 shows a conventional accelerometer module.
Figure 6:
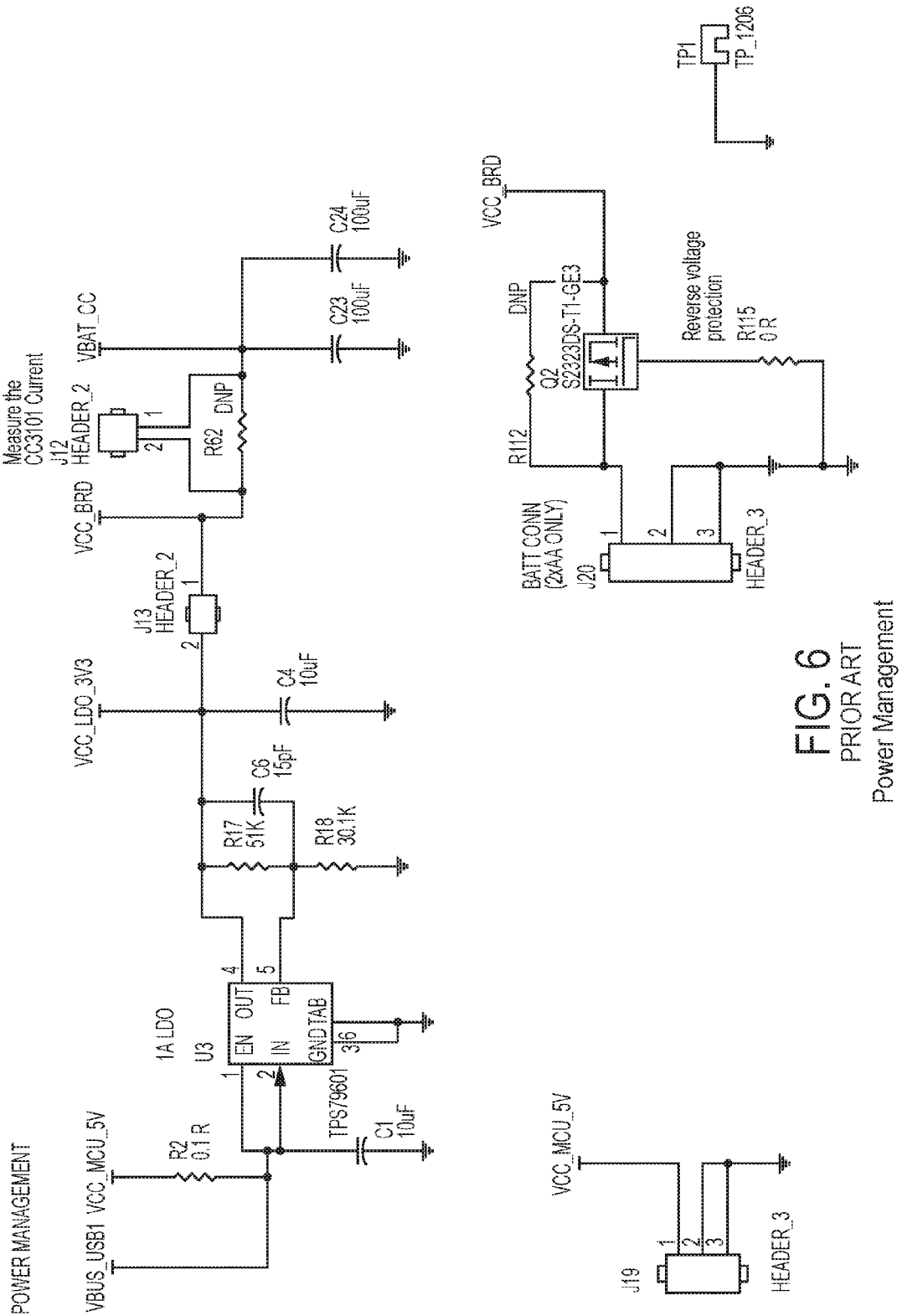
FIG. 6 shows a conventional power module.

FIG. 4A and FIG. 4B, taken together, are a schematic diagram of one embodiment of a first sensor hub according to principles of the disclosure. FIG. 4A shows a first part of the sensor hub, FIG. 4B shows a second part of the sensor hub. The core of the sensor hub module in the preferred embodiment is a conventional Cortex™ ARM M4 MCU with 802.11bg WiFi by Texas Instruments. The peripheral set includes SPI, UART, I2C, I2S, SDMMC, 4Channel ADC, 4 PWMs and built in power management. Crypto engines such as AES, 3DES, SHA and CRC enable safe connect to the Cloud. In certain embodiments, a Bosch BMA222 3-axis accelerometer, or the like, is mounted flat on the hub board shown in FIG. 5. In one embodiment, the power module, as shown in FIG. 6, is composed of a Texas Instruments TPS9601 single channel voltage regulator, a holder for two AA batteries and a Vishay MOSFET circuit to prevent flow in the wrong direction, along with related passive components.

The body-worn, implanted, and mobile components of the present wearable system (hereafter "the wearable") are highly reliable with long battery (or other mobile powersource, e.g. fuel cell) life, so that both the individual being monitored and those who may be required to intervene can rely on its continued operation over a sufficiently long period of time without the constant concern of power failure. To achieve this, an appropriate power source is selected and the electronics are engineered for low power consumption, particularly for processing and communications. Effective low-power engineering involves careful selection of electronic components and fine-grained power management so that particular subsystems (such as a communications radio, microprocessor, etc.) may, when appropriate, be put into a standby mode in which the power consumption is reduced to an absolute minimum, and then awakened when needed.

It is understood that a wearable needs to satisfy both cognitive and physical requirements to be useful. From a cognitive standpoint, the wearable needs to be simple to use, with as many functions as possible automated, so that the wearer can attend to other tasks with minimal cognitive burden imposed by the device. This is particularly important in the mutual self-help mode, where users monitor each other. To the extent that the user interacts with the wearable, the interactions must be carefully designed to minimize the frequency, duration, and complexity of the interactions. To the extent that the wearable interacts with the user, the interactions must be carefully designed to make the interactions appropriately intrusive. From a physical standpoint, the wearable's physical package needs to be as small and light as possible, and carefully positioned and integrated with other body-worn (or implanted or drone-carried or balloon-carried) elements so that it will not encumber the user, interfere with other tasks, or cause physical discomfort.

Even in situations where the signal of interest is measurable in a straightforward manner that does not burden or discomfort the user, the proper interpretation of this signal may require knowledge of other signals and the wearer's personal history. For example, it is relatively straightforward to measure the rate at which a person is taking steps. Added information such as the average length of steps by the individual, or like individuals, is required to know how rapidly a person is moving. As another example, the detailed eye and experience of a medical professional may be required at times to properly understand the meaning and physical information obtained from this invention.

Figure 7:
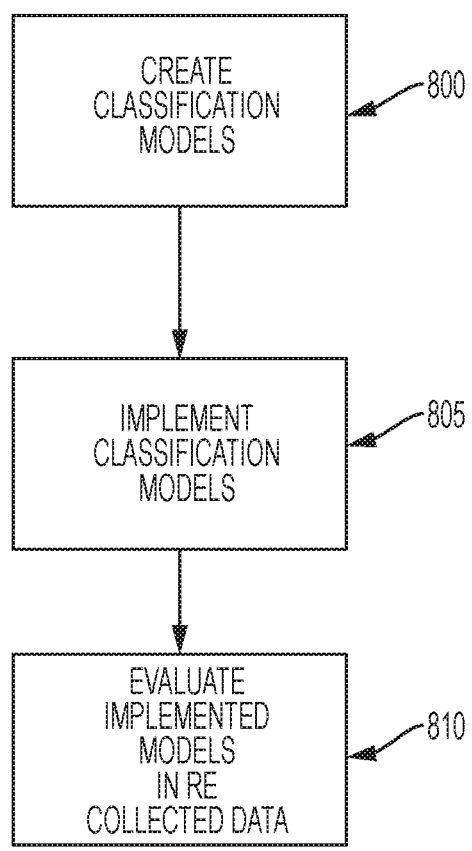
FIG. 7 shows a flow chart of a statistical classification process according to principles of the disclosure.

FIG. 7 shows a flow chart of a statistical classification process according to principles of the disclosure. Statistical classification is the process by which measured sensor data is transformed into class assignments and probabilities for a set of discrete classes of interest through the application of statistical classification techniques. The application of the process to the problem of fall prediction is one of the key innovations embodied in the present system. At step 800, an appropriate set of statistical classification models is created or re-created (hereafter to be called "model creation"). At step 805, the statistical classification models resulting from the model creation step are implemented on the wearable and/or server such that they can be evaluated in real-time using on-body and/or server-based computational resources ("model implementation"). At step 810, the wearable fall prediction system evaluates these models in real-time using live sensor data, the results of which may trigger communications with remote third parties, cause delivery of status information including alerts to the wearer and/or others, or otherwise play an important role ("model evaluation").

Model creation (step 800) may be done at least once for each class or individual user or set of data. In one embodiment of the disclosure, the data sets evolve by adding new data and new models almost indefinitely for individuals because they develop new or modified pathways for falling as they decline. Once a large general sample is developed, the model will be continually refined as the models are used (referred to as "on-line learning") and when the general sample is sufficiently mature, the corresponding statistical classifier can be embodied as an ASIC that is updated at some frequency. When real-time, on-line learning is not needed, the model creation process can be done off-line. Already-created models will require much less processing effort than their corresponding evolving models. The goal of the model creation process described here is to create statistical classification models that can be evaluated in real-time using only on-body resources.

Model creation starts with data gathering. In one embodiment of the disclosure, data is gathered through body-worn accelerometers. In general, this data is "labeled" so that what the data represents is known. In some embodiments, there are two data classes, such as "normal walking" and "walking toward a fall." Actual example data from both classes is gathered, although there are situations where simulated data may be used if the acquisition of real data is too difficult, costly, or poses some ethical or logistical challenges. From analysis of this representative data, appropriate modeling features are chosen to be used by the model. Features are then derived and measurements are computed from the "raw" sensor data. For example, derived measurements in one embodiment are created by computing the differential forward Fourier transform (DFFT) or power spectrum from a short-time windowed sequence of data. Features may also be derived by such means as bandpass filtering, signal integration or differentiation, computing the response of filter banks or matched filters, or other signal processing operations.

In some embodiments, there is a "trial feature" which is used to test possible model correlations. This analysis process typically includes the computation of several trial features in order to arrive at a final model feature. After features are chosen, an appropriate model type and structure is chosen. Finally, the parameters for the specific model type, structure, and representative data are estimated from the representative data.

The results of the individual model creation step (step 800) are: (1) the process for calculating model features, (2) the structure and type of the model, and (3) the model parameters themselves. These three elements specify the individual classifier. Implementing a model evaluation system (step 805) that is capable of evaluating the classifier in real-time using on-body resources is technically challenging. Feature calculation and model class posterior calculation (i.e., calculating the likelihood that an observed feature, or set of features, can be modeled by a particular model class) can be computationally intensive, but once it is done, the algorithm created is often very fast and makes efficient use of electronic resources.

The model created and implemented is part of a system capable of classifying "live" sensor data in real-time preferably using on-body resources according to the principles of the present disclosure. The step of classification (step 810) entails real-time comparison of the features and strings calculated from a data stream to the features, strings and parameters of the model. This matching using Bayesian or other statistics identifies the "movement behavior" with which the data stream best matches and yields a statistical estimate of the confidence for the match.

The results of this classification process drive the proactive communications features and may otherwise complement information acquired from the wearer. Such information includes the wearer's profile or history. Potential messages can include warning beacons of treacherous environmental situations for that user, beacons that lead users out of a potential or actual predicament in the environment, voice instructions, synthesized or recorded, and observations or human interventions by other people in central control or in the mutual self-help network.

Figure 9:
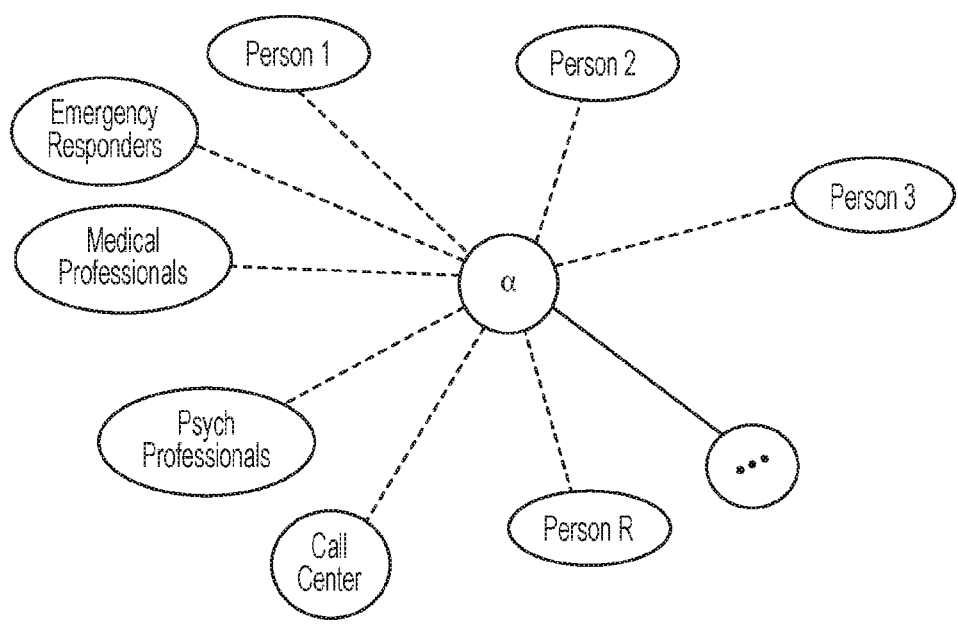
FIG. 9 shows one embodiment of a communitarian, mutual self-help model according to the principles of the present disclosure.

Having the capability to process information on-body is supplemented by the ability to send the original raw data, optionally labeled and optionally mediated by the results of on-body analysis, to other locations for further analysis or interpretation at a location remote from the body. Indeed, the capability to relay raw sensor signals, or their derivative products, to remote team members (for example in a communitarian, mutual self-help model as shown in FIG. 9), care givers, or rescuers may be important to the discussion, planning and execution of an appropriate intervention. As such, the distributed processing model need not be confined to on-body resources, as the wearable can participate in external networking, enabling communication with other team members, care givers, rescuers, etc.

As such, each type of participant may have a different view of the available data. Users (each a "Person" in FIG. 9) wear the device, which sends and receives information to and from the hub. Designated friends or caretakers can monitor another view to witness how their friend is doing without either having to be physically present or having state-of-art observation and intervention skills. An alternative view provides a history of the times the user was at heightened risk of a fall. For example, elderly people take walks when they are able, or when they have a walking partner. The present inventive device and system could make it possible for them to take a walk when it is not feasible for the monitoring person to be physically present. Furthermore, a single person can monitor several walkers. This feature is particularly valuable for medical professionals who are provided a special view that optionally even enables them to see summaries of events of concern, to supplement real time monitoring. In this way they are enabled to use their time efficiently and effectively with Persons under their care. Optionally, a voice communication system may be included in the device as an alternative to typical cellular phone communications. A system of views with suitable security guarantees that participants have access only to information to which they have been granted access.

Such communications can be expensive in terms of power consumption, and are generally not preferable for routine operation, although emerging battery technology and increasing acceptance of weight reduces resistance by users. This radio channel is, however, important to push data out to processing resources such as remote computer servers. These servers can be used to provide more sophisticated analysis, requiring computer resources and power that are not reasonably placed on-body today, although it is expected that more resources will be shifted to the body as computer resources and power expand.

In one embodiment of the disclosure, sensor information is input to a DFFT algorithm, which computes the Fourier Transform as output. Such transformation of the original data into the frequency domain aids data analysis particularly in cases in which all or part of the phenomena are fundamentally oscillatory. Examples of such oscillatory data are ambulatory motion, heartbeat, breathing, and motion on a vehicle that is traveling. This output is then input to a classifier module, which analyzes and recognizes the pattern or patterns inherent in the data and compares them to patterns the system has been trained to recognize using a statistical algorithm. The classifier module output consists of one or more matched patterns along with the confidence level for the match.

The embodiment described above is merely exemplary. Other sets of functions may be used instead or in addition. For example, shifting to another set of orthonormal basis vectors that sufficiently span the physical space or smoothed manifold is considered to be within the scope of the present disclosure.

The simplest display of output information in the presently preferred embodiment is a simple audible tone to alert users when they are at particular risk of an emergent fall. A more complicated display of the output information in the presently preferred embodiment is a listing of patterns matched along with confidence levels. For users with adequate hearing, the message can be converted to a simple voice message, and when asked for, a complete voice synthesis of key information. Those skilled in the art will recognize that many alternative displays are possible and can be useful.

The manner in which the information is visualized is supportive of the core feature of "alerting" based on the output of the classifier(s). The core feature of the "proactive monitor" is that it is proactive. In some embodiments of the disclosure, nothing is displayed until a fall risk classifier detects that there is a noteworthy risk, and seeks to alert the wearer as well, possibly, as other people. This can be extended to very advanced notification. For example, if central management notices that there is this particular day a large number of people in a community are making frequent stumble steps, it may elect to notify first responders so that there are likely to be enough personnel to address an increased number of falls for that day.

In a further alternative embodiment, a motion analysis monitor system analyzes movement in order to determine if the monitored person requires assistance. The system is capable of assessing the general activity level of the user and tracking his or her activity level over time, providing information to healthcare professionals, caregivers, and mutual self-help participants such as is shown in FIG. 9. Furthermore, the motion analysis monitor system can include an automatic fall detection feature and a caregiver notification feature for individuals who are at increased risk of falling, such as the elderly, handicapped, and the infirm. In addition, the monitor can provide a manual call button feature that will enable monitored individuals to notify caregivers in the event emergency assistance is needed, whether in advance of a possible fall, or after a fall has occurred.

Figure 8:
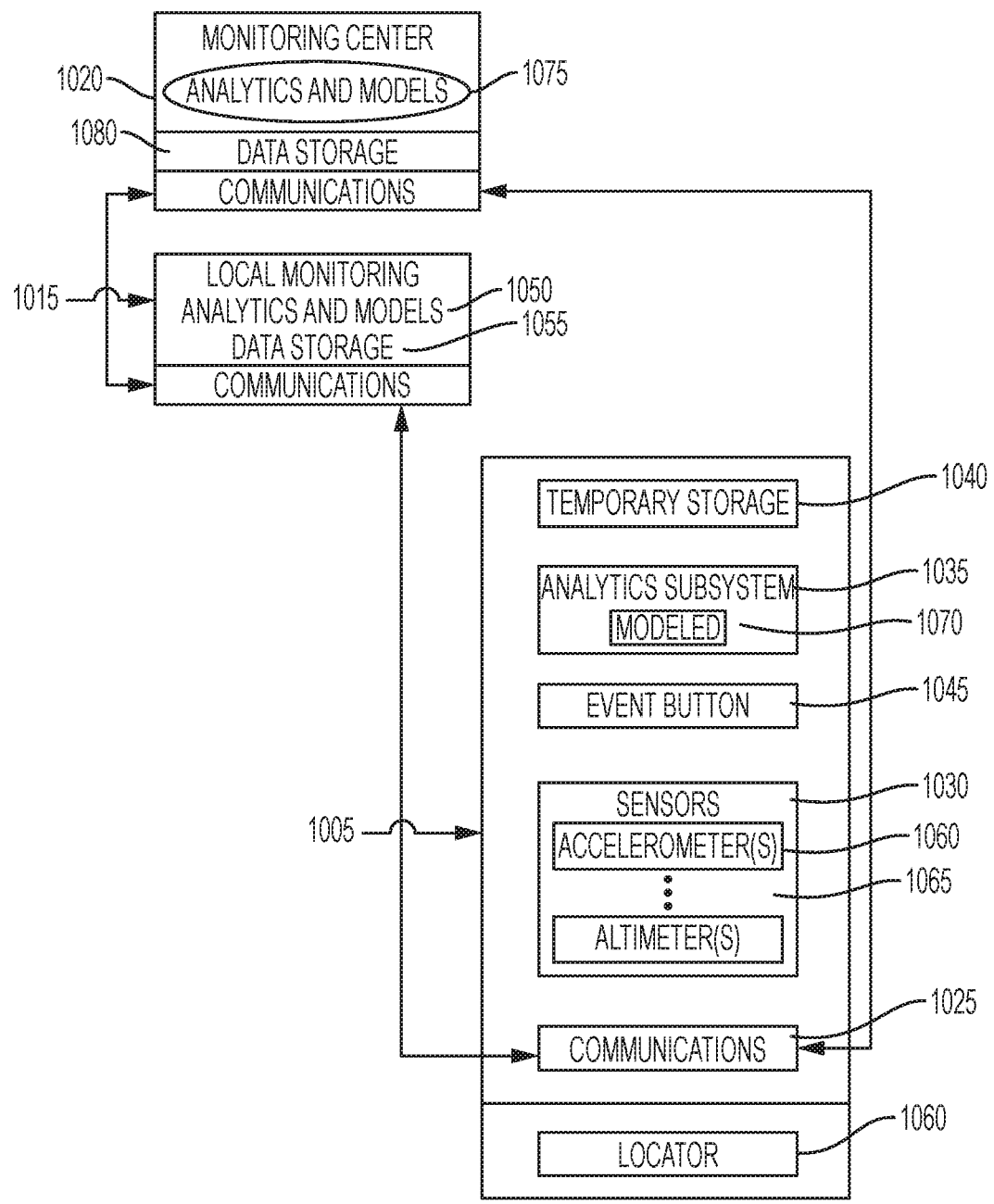
FIG. 8 shows a block diagram of one embodiment of a motion analysis monitor system of the present disclosure.

FIG. 8 is a block diagram of one embodiment of a motion analysis monitor system 1000. The monitor system 1000 includes a wearable monitoring device 1005 that is configured to be worn by a person. The wearable monitoring device 1005 communicates 1025 via means such as a cell phone network, a wireless community network, or via a Cloud connection, with a monitoring center 1020 that optionally provides administration for the system 1000 and optionally passes alerts to caregivers.

The wearable monitoring device 1005 is typically configured for constant and long-term wearing by a person in need of motion monitoring. Although the sensor subsystem 1065 included in the wearable monitoring and prediction device 1005 could be worn on the body in a variety of locations, the device 1005 is preferably located somewhere on the torso rather than an extremity. Locating a fall-related sensor on an extremity generally increases the number of degrees of freedom, increasing the difficulty of rejecting false positives and negatives, and providing a new class of false positives. False positives for fall prediction, however, do not pose the same cost problems as do false positives for fall detection, because the latter do not require automatic response by an EMT unit, for example.

Still referring to FIG. 8, the wearable monitoring device 1005 may alternatively take many forms and assume many locations. It should be understood that all configurations of the wearable monitoring device 1005 are addressed within the scope of the disclosure. In an alternative arrangement, the on-person device 1005 has a locator 1060 which is, for example, a GPS device. As described herein, the data from a daily buffer can be loaded to the server whenever a fall event is detected or manually identified by the user. Data may also be uploaded more frequently as a result of other criteria such as a periodic clock event.

In another embodiment, data can be captured and analyzed in either analog or digital format. Consider for example a "correction step" which occurs as a result of people perceiving that they are out of balance and needing to deviate from their normal gait to avoid getting further out of balance and perhaps falling. Using x, y, z coordinates with z normal to the ground, and x the path for walking, the correction step may take place partly or entirely in the y direction and may include a pause of motion in the x-direction. If the path is along the x-axis in this coordinate system, there is a sudden increase in the value for y and also for acceleration in the y direction. There is also a pause or deceleration in the x-direction while people regain perceived stability. Using an analog accelerometer, the output voltages for the y-direction and the x-direction can pass through a pair of comparators such as the LTC6702 by Linear Technology to determine if the y-acceleration exceeds an individual's threshold value for a side step and the x-acceleration goes negative. The output of the comparator for the y-direction is one of two values, 1 if the acceleration exceeds the threshold, 0 if it does not; that is, 1 if there is heightened risk of a fall, 0 if there is not. The output of the comparator for the x-direction is also one of two values, 1 if the acceleration equals or exceeds a set value less than zero, 0 if it is less than that threshold less than zero; that is 1 if there is no unusual risk of a fall in this scenario, 0 if there is. Further electronics circuitry can also be set up to determine whether these events are associated, in the sense that they have effect in the same time window.

A useful statistic is the total number of such events as counted by an asynchronous circuit over a monitoring time such as an hour or a day. If this number is zero or small, it is not cause for concern. If this number is large, a suitable medical professional may elect to treat it with concern. When the number first begins to increase, for example, the person may be directed to the kind of balance (exercise) class that has been promulgated by the National Institute on Aging, and this is likely to be fully sufficient, as determined by a medical professional.

Another embodiment of the system of the present disclosure uses a sequence of acceleration thresholds and parameters to determine non-statistically whether a fall has occurred by using the streaming output of the accelerometer. Thus, there are at least three means for harvesting data to be used to populate the input sample domains for the present statistical classification approach. First, is by collecting buffered data (1040 in FIG. 8) on the historical accelerometer readings whenever the automatic fall detection criteria are met as determined by the analytic subsystems (1035, 1050, 1070, 1075). These criteria are optionally simplified, as discussed below, so that false positives and false negatives are included in the sample. Second, is by providing for and setting values for a second set of criteria using the analytic subsystem (1035, 1070) in the same device, and uploading the contents of the log (1040 in FIG. 8) when these criteria are met. In this manner it is possible also to measure strings that are labeled as near-falls. Third, is a data stream (1040 and 1025 in FIG. 8) resulting from this data harvesting approach is identified as triggered when users press their HELP button (1045 in FIG. 8). A fourth data stream is enabled by significantly increasing the size of the data buffer (1040 in FIG. 8). If the pre-fall buffer is increased to hold a minimum of about five minutes of data, then the approximate time of a fall can be remembered, and searched for in the data, and followed up by discerning the precursors to the fall. Additionally, a caregiver or bystander can press the HELP (1045 in FIG. 8) button well after the fall has occurred, leading to a later search for the appropriate fall string. Note that on-body data storage (1040) is very limited, containing sensor data only between candidate events, when it is uploaded to the local data storage (1055). At regular times that local data is uploaded and synchronized with the data in the main remote server (1080), where it is used to create models, including models based on Big Data techniques.

In the initially preferred embodiment, a 30 to 60 second first-in, first-out (FIFO) buffer of streaming acceleration data is maintained constantly as the device operates. People skilled in the art and the process of falls and falling will recognize that 30 to 60 seconds is an approximate initial number representing adequate time to gather pre-fall data of significance balanced against creating a burden by gathering too much data for current electronics, battery charge densities, and network communications. Longer and shorter buffer sizes should be seen as equivalent in terms of the substance of this disclosure. In general however, the buffer should hold at least ten seconds of data. In a related system by Applicant, as seen in U.S. Pat. No. 8,217,795, this produces a buffer size of less than 2 megabytes.

In certain embodiments of the present system, there is a pre-fall buffer and an identical post-fall buffer to diary the accelerometer output. That is, with two sets of parameters, falls and near-falls, alone or in combination, can trigger labeling and sending the contents of one or both buffers to permanent internal storage such as SD card or equivalent, external on-board storage such as SD or equivalent, external server, or the Cloud.

This data transmission includes three components of acceleration, date/time, a fall indicator, and an identifier for the user. In some cases, it also includes global position as determined by GPS position and orientation. The same transmission could include other or redundant information such as the global position as determined by triangulation of cell towers. In the present embodiment, this information is sent by email or SMS to a specific receiving account. In another embodiment, it would be transferred directly or indirectly to a Cloud account or other optionally secure repository. In yet another embodiment, it would be retained or transferred directly or indirectly to a suitable wearable computer or other optionally secure device that can be networked with the necessary processing power, storage, and speed/response times. A bank of virtual servers with at least one server always operating and quick automated start-up of additional servers in response to demand patterns serves the need well for response times well under one second, usually under one-tenth of a second.

U.S. Pat. No. 8,217,795, by Applicant, describes an impact, or a fall condition and then an impact, which are crude initial indicators of a fall. Both are parameterized in the automated fall evaluation. In contrast, the present disclosure is focused on predicting falls. In the data gathering phase of populating the database for setting up this fall prediction device, it is desirable to include both fall events and false fall events, the class of which is preferably verified by voice communication with a call center. Falls, near-falls, false positives, and false negatives can be determined by prompt call center follow-up. Therefore the stages after a fall to eliminate insignificant or false falls can be eliminated by setting the parameters appropriately. Even the falling condition at the beginning can be eliminated during this stage of verification by call center personnel. Call center contact with the fallen person can also be used to accurately label a string as a fall or non-fall, although it is useful to retain both evaluation labels when they are available. Call center activity is expensive, so it is desirable to reduce it over time by relying on automated means as much as reasonable. Of course that is in part the point: by anticipating and eliminating falls, call center activity is correspondingly reduced.

A fall prediction repository constitutes a database of string information about falls, non-falls, and near-falls for each user. It can therefore be a utility for a Big Data approach to fall prevention. The contents of such a database can be used, for example, as part of the input for a SVM. In one embodiment, a boosted version uses a group of machine learning and recognition mechanism machines, some optionally digital computerized and others analog, each in its own domain of best performance, to determine whether an individual person is currently exhibiting a pattern of movement that indicates a fall is emergent. The system may also use optional information about the likelihood of that fall and the type of fall. Further, the system may also include likely medical impacts of a fall even before it happens. Eventually, this information can be used to devise trainings to teach physical and cognitive strategies that people can learn and train their bodies to use. An everyday example is walking on icy streets and sidewalks in cold climates. Some people's bodies learn from experience how to slip wildly and recover without falling. By way of example, an athlete slipped and fell on a wet spot on the court, his left leg remained straight, and his right knee took the strain of the fall, striking the court on its inside such that his two legs were splayed apart. The athlete felt a "tweak" inside his right knee, and after examining an MRI, doctors decided he should not play for two weeks. If he had not made an early commitment to rely on his left leg to sustain his balance, or if he had used the slipperiness early to enable him to pull his legs together earlier rather than pushing off his left foot, so that he relied strategically on both legs rather than just one leg, this might have been a fall on his right side or possibly a near-fall event instead of a fall event. Such observations, analysis, and computerized physical modeling can provide particularly useful supplemental data for the device described in this application, leading to many other uses.

The approach of this disclosure is to be able to discern many of the details for such a fall, and the space-time string of the sensors. In some cases, this information is supplemented by body orientation, to be stored in the database space to be compared to other falls by the machine learning algorithm. For example, the athlete's slip without the impact of a step would indicate that this started the fall process; the timing of the impact of the knee on the floor would be expected to indicate whether it was the right knee or the left knee that struck the floor. A suitably sensitive accelerometer might discern that there was a "tweak" inside the athlete's right knee, and the pattern of feet impacting the floor long in advance would indicate whether his recently sprained ankle placed him at significantly increased risk of a fall. The reader is warned not to interpret this example too literally, as it is described in a classical deterministic reality whereas classification is done with a significant sample size in a deeply statistical reality that is expected to yield more useful and higher quality matches between relevant string clusters in the database and events in the physical world.

The overall contents, as well as subsets, of this repository provide a database that is used as part of the input for a SVM or other machine learning and recognition mechanism to determine broader group criteria as to whether an individual person is currently exhibiting behavior that indicates a fall is emergent. When a match occurs, the user or a helper is alerted to change the behavior and thus avoid the fall. Partly as a result of successful intervention, many falls will be avoided. Instead of a tally of falls by type, there will be a tally of fall classes that were avoided. This is useful, as stated, for avoiding falls. It is also useful as input for health professionals who can use this information for patient evaluation, and can design therapeutic interventions to reduce risk of those particular pathways to falls. For example, it has already been discovered that weak ankle ligaments and muscles leads to instability, so that physical therapists specify and teach exercises to strengthen those muscles and ligaments before the risk of a fall becomes unacceptably great.

When emergent fall behavior is identified, a variety of real-time interventions can alert users. These may range from an alarm to warning the user to interrupt that behavior (e.g., for a walker who takes several correction steps in a minute, the fix might range from walking with much greater care to walking with a cane to taking a time-out by sitting down for a minute) to deployment of a device to catch the user and actively prevent the fall to voice instructions requesting passers-by to tend to the person to avoid a fall. The alarm and voice components are adjustable in such dimensions as type and loudness so as to be suitable for the user and situation. It is particularly important that the alarm appropriately catch the user's attention in a way that leads to effective action to avoid a fall, while at the same time not being so distracting as to trigger or otherwise contribute to a fall.

Because this method is predictive, often yielding a warning with more than a second to spare before a fall commences, there is extra time, relative to other approaches, to allow a relatively slow or distracted person's mind to respond or a relatively slow prevention device to deploy. If the advanced notification occurs long enough before a fall would happen, the user can even overcome a startle reaction to the alarm, recover, and change behavior to avoid the fall.

In yet another embodiment, visual information and possibly other sensory-equivalent information is stored in a repository and used in machine perception of potential circumstances that would produce falls. This visual information can be either part of the N-dimensional data string stored in the database, or associated to a fall indicator string, depending on such variables as how a particular classifier is set up for a particular embodiment of the disclosure. In some embodiments, the data string includes x, y, z components of orientation as measured using GPS, time, and x, y, z components of acceleration; one or more metrics to characterize whether a fall resulted, and if so, what type of fall. For example, visual classification is capable of determining gross unevenness of sidewalk pavement as well as the pace at which a user is walking or running on the sidewalk. If the device of the present disclosure detects such a risk, it is able to predict that, for example, the fall is likely to be a trip-and-fall with most likely damage to the wrists, and lesser risk to the knees and head. The system can provide a warning signal so the person can avoid the fall, or so that impact prevention technologies can deploy to reduce the damage from the fall.

Limited information about falls can also be uploaded to repositories such as Google Maps. In some cases multiple falls will accumulate in particularly risky locations. Users can carry with them a device that reads this information and warns such approaching users when at least a threshold number of falls has occurred there. If there is a suitable information layer created for such a map, users can also review their route for risks before they take that route.

In certain embodiments, the database stores each string with a unique identifier for the user who produced that string. Each user also has an optionally encrypted table of individual information such as birthdate, weight, height, body mass index, and other information that is likely to be useful in interpreting raw data. If a person had broken her ankle falling on poor walkways with holes, then also during the time until full recovery, that resulting vulnerability would be entered into the string, so that there is indication of it and the recognition system is aware of the likelihood of re-injury. For example, people who are obese might be expected to be more vulnerable to a fall than a person who is of "normal" weight. In this, as elsewhere, strings stored in the database might be normalized to fit into a general classification algorithm. It should be noted also that the data can optionally be stored in $4^{th}$ normal form.

Applicant's own previous work relates to the formulation of a deterministic and statistical approach to automatic detection of falls. The two approaches are applicable in fall prevention in some respects. In fall detection, there is a limited number of degrees of freedom. Most people who fall are not gymnasts or divers who can perform a "full twisting 1½ somersault," so freefall is defined as the same for everyone who falls. Typical impact is often measured use-fully with three data points worth of acceleration and time data. With this kind of data it may be simpler to use a substantially deterministic algorithm to determine whether those data points represent a fall.

On the other hand, fall prediction and fall prevention are inherently more statistical in nature, requiring machine learning and perception. A minimum of three hundred data points in each buffer, pre-fall buffer, and post-fall buffer implies the possibility of detecting a large number and variety of motions. Each motion represents a possible pathway to a fall, each with its own probability or likelihood in general or for that specific person. The likelihood of a fall is the appropriate weighted sum of likelihoods of the relevant pathways at this particular time. Therefore, the preferred embodiment uses statistical machine learning to predict falls. This should not be construed to mean that the Applicant rejects deterministic algorithms to predict falls.

The computer readable medium as described herein can be a data storage device, or unit such as a magnetic disk, magneto-optical disk, an optical disk, or a flash drive. Further, it will be appreciated that the term "memory" herein is intended to include various types of suitable data storage media, whether permanent or temporary, such as transitory electronic memories, non-transitory computer-readable medium and/or computer-writable medium.

It will be appreciated from the above that the invention may largely be implemented as computer software, which may be supplied on a storage medium or via a transmission medium such as a local-area network or a wide-area network, such as the Internet. It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

While various embodiments of the present invention have been described in detail, it is apparent that various modifications and alterations of those embodiments will occur to and be readily apparent to those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having," and variations thereof herein, is meant to encompass the items listed thereafter and equivalents thereof as well as additional items while only the terms "consisting of" and "consisting only of" are to be construed in a limitative sense.

The foregoing description of the embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

A number of implementations have been described. Nevertheless, it will be understood that various modifications may be made without departing from the scope of the disclosure. Although operations are depicted in the drawings in a particular order, this should not be understood as requiring that such operations be performed in the particular order shown or in sequential order, or that all illustrated operations be performed, to achieve desirable results.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed:

1. A system for detecting an emergent fall comprising:
one or more sensors wearable by one or more users, at least one of the one or more sensors being configured to collect and transmit sensor data, including motion data;
a hub for receiving and labeling the sensor data, wherein labeling the sensor data includes date/time and whether a subsequent fall actually occurred;
a processor on the hub configured to:
classify the sensor data as a data classification including at least whether a fall is emerging or not according to a fall prediction model;
store the data classification, wherein the labeled sensor data is used to create one or more parameters, strings, features, data models, and classes to be used in subsequent data classification via supervised or unsupervised machine learning;
process one or more parameters, where the one or more parameters include time duration and time placement for the one or more strings;
process one or more strings, where the one or more strings comprise one or more streams of sensor data including N-dimensional event phase space information which can be matched to behavioral motion, such that the one or more strings are classified into one or more classes and the one or more classes are used to determine individual and group thresholds used by an alert system; and
match output from the data classification with the one or more parameters, strings, features, and data models from the fall prediction model; and
a transmitter for transmitting information to the alert system and to a repository of data for use by the fall prediction model;
the alert system being configured to send a notification that a risk of a fall is above a threshold based, in part, on a confidence level for a match to the one or more parameters, strings, features, and data models from the fall prediction model to the data classification.

2. The system for detecting an emergent fall of claim 1, wherein the at least one sensor is an accelerometer.

3. The system for detecting an emergent fall of claim 1, wherein the notification is in the form of an audio signal.

4. The system for detecting an emergent fall of claim 1, wherein the notification is in the form of a visual signal.

5. The system for detecting an emergent fall of claim 1, wherein the notification is in the form of tactual/vibratory signal.

6. The system for detecting an emergent fall of claim 1, further comprising a receiver for receiving data from the repository of data for further use by the fall prediction model.

7. A method of detecting an emergent fall comprising:
providing at least one wearable sensor on at least one user;
measuring at least motion data with the at least one sensor;
creating a fall prediction model, wherein an input for the fall prediction model comprises at least the motion data and time data;
implementing the fall prediction model;
comparing at least one stream of sensor data including N-dimensional event phase space information of the motion data with at least one stream of sensor data including N-dimensional event phase space information of the fall prediction model, wherein the at least one stream of sensor data can be matched to behavioral motion, such that the at least one stream of sensor data is classified into one or more classes and the one or more classes are used to determine individual and group thresholds used by an alert system;
creating a data classification including at least whether a fall is emerging or not using the comparison of at least the motion data and optionally the time data to the fall prediction model;
calculating a probability that, and a time frame within which, a fall is emergent;
calculating a confidence level for the probability that a fall is emergent;
indicating whether the fall is emergent based, in part, on the data classification;
evaluating the fall prediction model in real-time;
evolving the fall prediction model with additional data from the at least one sensor on at least one user;
determining if the fall is emergent based, in part, on whether a risk of a fall is above a threshold; and
communicating a notification with the alert system, if the fall is emergent, that the fall is emergent so that the fall can be prevented.

8. The method for detecting an emergent fall of claim 7, wherein the at least one sensor is an accelerometer.

9. The method for detecting an emergent fall of claim 7, wherein the notification is in the form of an audio signal.

10. The method for detecting an emergent fall of claim 7, wherein the notification is in the form of a visual signal.

11. The method for detecting an emergent fall of claim 7, wherein the notification is in the form of a tactual/vibratory signal.

12. The method for detecting an emergent fall of claim 7, further comprising a receiver for receiving data from a repository of classified data for further use by the fall prediction model.

13. The method for detecting an emergent fall of claim 7, further comprising adjusting threshold parameters to adapt the fall prediction model to modify a sensitivity of the fall prediction model for the at least one user.

14. A wearable for detecting emerging falls and an actual fall comprising:
a power source;
one or more sensors wearable by at least one user, at least one of the one or more sensors being configured to collect and transmit at least motion data;
at least one processor for classifying at least the motion data and time data received from the one or more sensors according to a fall prediction model, such that data classification includes at least whether a fall is emerging or not;
one or more hubs configured to:
receive raw sensor data and the classified data as well as information about the data classification,
process one or more parameters including time duration and time placement for one or more strings, where the one or more strings comprise one or more streams of sensor data including N-dimensional event phase space information which can be matched to behavioral motion, such that the one or more strings are classified into one or more classes and the one or more classes are used to determine individual and group thresholds used by an alert system: and
transmit the information about the classification to the alert system;
a communications system capable of sending data and commands, as well as information contributing to sending alerts between a remote server, a local server and the one or more hubs; and
the alert system for sending a notification when an emergent fall has been identified based in part on whether a risk of a fall is above a threshold based on the data classification by the fall prediction model.

15. The wearable for detecting a fall of claim 14, wherein the at least one sensor is an accelerometer.

16. The wearable for detecting a fall of claim 14, wherein the notification is in the form of an audio signal.

17. The wearable for detecting a fall of claim 14, further comprising a receiver for receiving data from a repository of classified data for further use by the fall prediction model.

18. The wearable for detecting a fall of claim 14, further comprising a machine learning server to offload demand from the one or more hubs and to function as a data repository to optionally implement a Big Data-based approach to creation and evolution of data models, features, and parameters for use by the fall prediction model.

19. The wearable for detecting a fall of claim 18, wherein the machine learning server runs in a communitarian mutual self-help mode with different views of individual and group data:
to enable use of one or more models, thresholds, and/or parameters by at least one user to identify actionable likelihood of falls;
to enable mutual monitoring and help by the one or more participating users;
to enable privacy by the one or more users;
to enable monitoring and data acquisition by professionals serving patients or participating users;
to enable record keeping of the one or more users; and
to enable communications among the professionals and the one or more participating users using the communitarian system.

20. The system for detecting an emergent fall according to claim 1, wherein a false positive and a false negative may appear as a pause in motion between 0.5 second and 5 seconds, with false negatives being closer to 0.5 seconds and false positives being about 5 or more seconds.

* * * * *